US012575988B2

(12) United States Patent
Stashuk et al.

(10) Patent No.: US 12,575,988 B2
(45) Date of Patent: Mar. 17, 2026

(54) SYSTEM, METHOD, AND COMPUTER ALGORITHM FOR CHARACTERIZATION AND CLASSIFICATION OF ELECTROPHYSIOLOGICAL EVOKED POTENTIALS

(71) Applicant: SafeOp Surgical, Inc., Carlsbad, CA (US)

(72) Inventors: Dan Stashuk, Stamford, CT (US); Richard A. O'Brien, Hunt Valley, MD (US)

(73) Assignee: ALPHATEC SPINE, INC., Carlsbad, CA (US)

( * ) Notice: Subject to any disclaimer, the term of this patent is extended or adjusted under 35 U.S.C. 154(b) by 206 days.

(21) Appl. No.: 18/340,753

(22) Filed: Jun. 23, 2023

(65) Prior Publication Data

US 2023/0329948 A1     Oct. 19, 2023

Related U.S. Application Data

(60) Continuation of application No. 16/543,987, filed on Aug. 19, 2019, now Pat. No. 11,684,533, which is a (Continued)

(51) Int. Cl.
| | |
|---|---|
| *A61B 5/24* | (2021.01) |
| *A61B 5/00* | (2006.01) |

(Continued)

(52) U.S. Cl.
CPC ............... *A61G 13/02* (2013.01); *A61B 5/24* (2021.01); *A61B 5/246* (2021.01); *A61B 5/377* (2021.01); *A61B 5/383* (2021.01); *A61B 5/388*

(2021.01); *A61B 5/4041* (2013.01); *A61B 5/4821* (2013.01); *A61M 16/01* (2013.01); *A61N 1/3605* (2013.01); *A61B 5/021* (2013.01);

(Continued)

(58) Field of Classification Search
CPC ........... A61B 5/24; A61B 5/245; A61B 5/377; A61B 5/383; A61B 5/388; A61B 5/4041; A61N 1/3605; A61N 1/30617
See application file for complete search history.

(56) References Cited

U.S. PATENT DOCUMENTS

| | | | | |
|---|---|---|---|---|
| 5,343,870 A | * | 9/1994 | Gallant | ................. A61B 5/276 |
| | | | | 600/524 |
| 2004/0010203 A1 | * | 1/2004 | Bibian | .................. A61B 5/726 |
| | | | | 600/544 |

(Continued)

OTHER PUBLICATIONS

S Kalson Maximum Likelihood Estimator of Signal-to-Noise Ration and Combiner Weight, NASA TDA Progress Report 42-85; Jan.-Mar. 1986 pp. 32-42 (Year: 1986).*

*Primary Examiner* — Brian T Gedeon
(74) *Attorney, Agent, or Firm* — Dentons Durham Jones Pinegar; Sarah W. Matthews

(57) ABSTRACT

An automated EP analysis apparatus for monitoring, detecting and identifying changes (adverse or recovering) to a physiological system generating the analyzed EPs, wherein the apparatus is adapted to characterize and classify EPs and create alerts of changes (adverse or recovering) to the physiological systems generating the EPs if the acquired EP waveforms change significantly in latency, amplitude or morphology.

16 Claims, 11 Drawing Sheets

Stimulation of a Physiological System

Context Relevant Stimulus ➡ Physiological System of Interest ➡ Electrophysiological Response

Related U.S. Application Data division of application No. 13/874,867, filed on May 1, 2013, now Pat. No. 10,391,012.

(60) Provisional application No. 61/641,583, filed on May 2, 2012.

(51) Int. Cl.

| | |
|---|---|
| *A61B 5/246* | (2021.01) |
| *A61B 5/377* | (2021.01) |
| *A61B 5/383* | (2021.01) |
| *A61B 5/388* | (2021.01) |
| *A61G 13/02* | (2006.01) |
| *A61M 16/01* | (2006.01) |
| *A61N 1/36* | (2006.01) |
| *A61B 5/021* | (2006.01) |

(52) U.S. Cl.
CPC ............. *A61B 5/4833* (2013.01); *A61B 5/704* (2013.01); *A61B 5/7246* (2013.01); *A61B 5/7264* (2013.01); *A61B 5/746* (2013.01); *A61B 5/747* (2013.01); *A61B 2505/05* (2013.01); *A61M 2230/16* (2013.01); *A61N 1/36017* (2013.01)

(56) References Cited

U.S. PATENT DOCUMENTS

| | | | |
|---|---|---|---|
| 2005/0119711 A1* | 6/2005 | Cho ..................... | A61B 5/0816 |
| | | | 607/42 |
| 2010/0312124 A1* | 12/2010 | Johnson ................ | A61B 5/746 |
| | | | 600/587 |
| 2011/0230785 A1* | 9/2011 | Higgins ................ | A61B 5/486 |
| | | | 600/554 |
| 2016/0270679 A1* | 9/2016 | Mahon .................. | A61B 5/388 |

* cited by examiner

Stimulation of a Physiological System

Acquiring Evoked Potentials
Each system is stimulated with a series of stimuli:
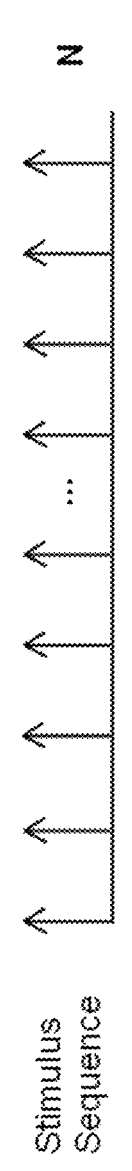
Stimulus Sequence
Which causes a series of electrophysiological responses that can be detected at specific sites:
Response Sequence
FIG. 2

The response sequence is ensemble averaged
to get a final ensemble averaged evoked potential (EP).

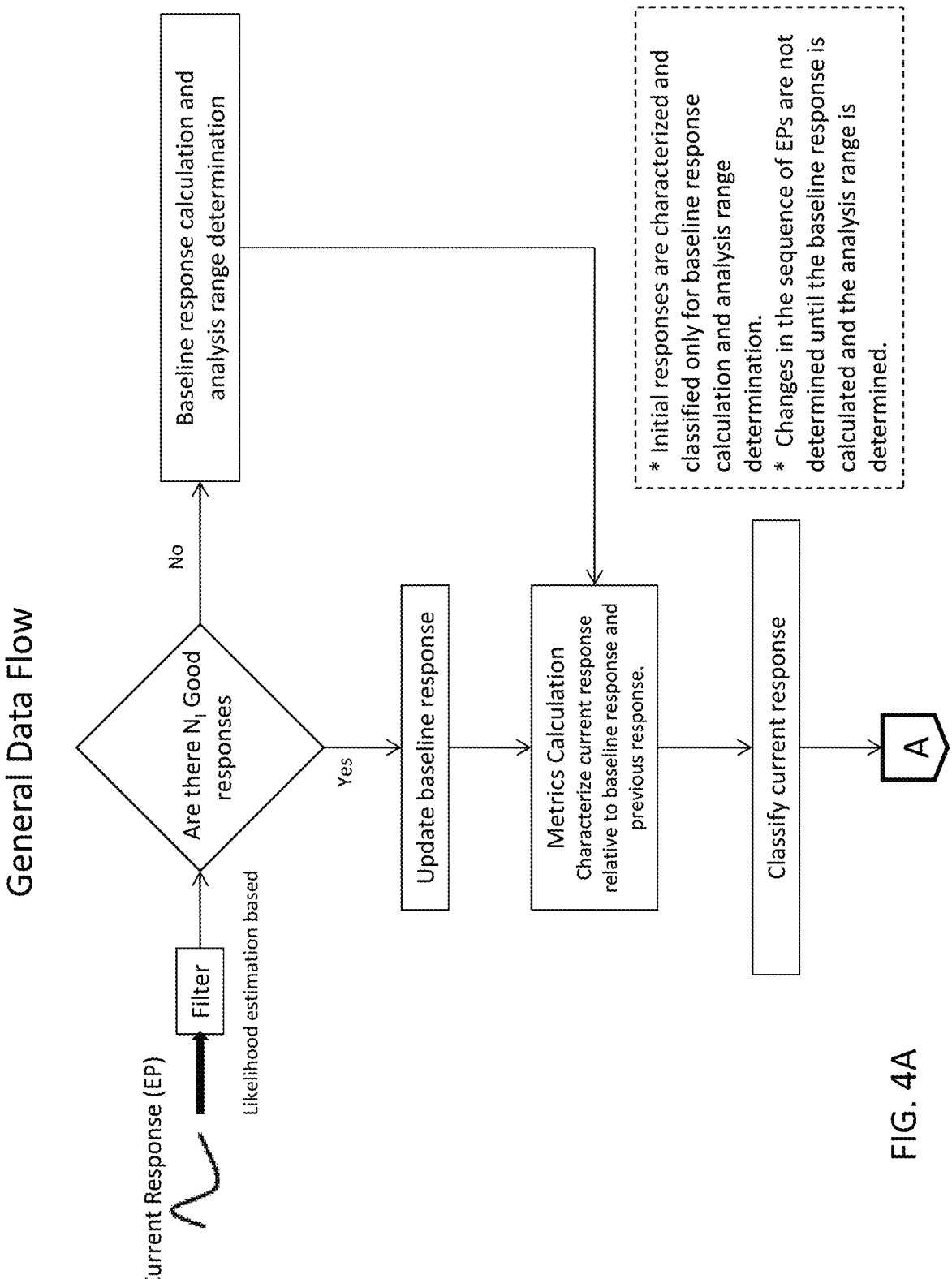

General Data Flow

Current Response (EP)

Filter

Likelihood estimation based

Are there N₁ Good responses

No

Baseline response calculation and analysis range determination

Yes

Update baseline response

Metrics Calculation
Characterize current response relative to baseline response and previous response.

Classify current response

A

* Initial responses are characterized and classified only for baseline response calculation and analysis range determination.
* Changes in the sequence of EPs are not determined until the baseline response is calculated and the analysis range is determined.

FIG. 4A

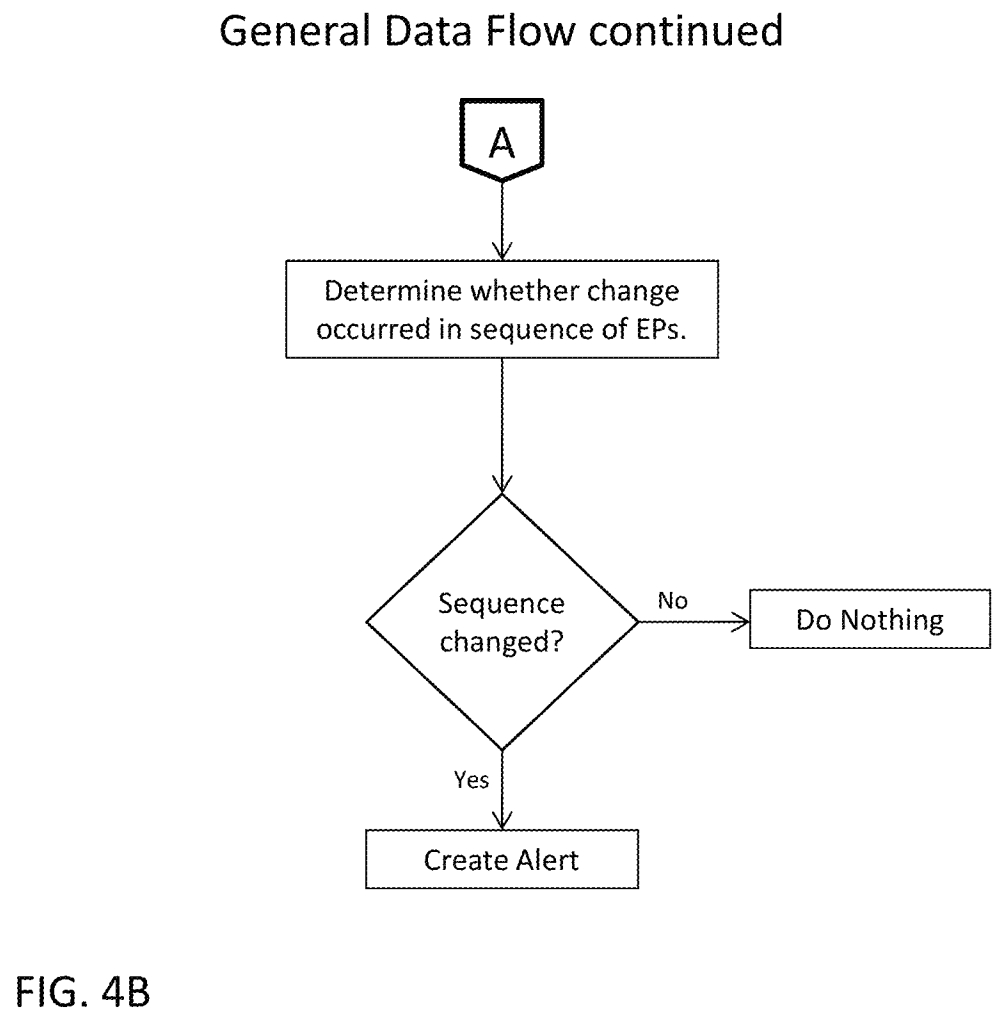

General Data Flow continued

A

Determine whether change occurred in sequence of EPs.

Sequence changed?

No → Do Nothing

Yes → Create Alert

FIG. 4B

Baseline Response Calculation and Analysis Range Determination

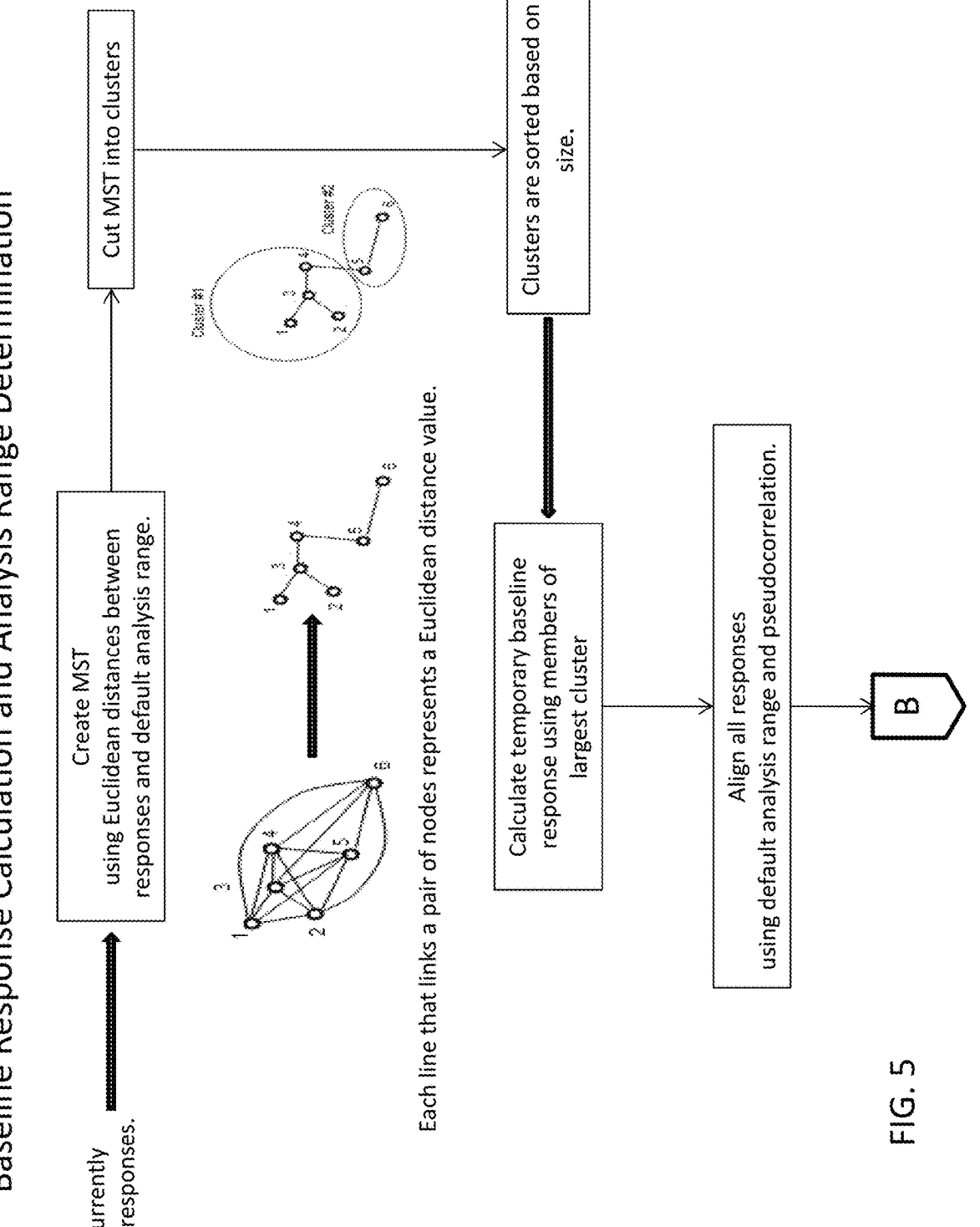

All currently loaded responses.

Create MST using Euclidean distances between responses and default analysis range.

Cut MST into clusters

Each line that links a pair of nodes represents a Euclidean distance value.

Clusters are sorted based on size.

Calculate temporary baseline response using members of largest cluster

Align all responses using default analysis range and pseudocorrelation.

SYSTEM, METHOD, AND COMPUTER ALGORITHM FOR CHARACTERIZATION AND CLASSIFICATION OF ELECTROPHYSIOLOGICAL EVOKED POTENTIALS

CROSS REFERENCE TO RELATED APPLICATION

This application is a continuation application of U.S. patent application Ser. No. 16/543,987, filed Aug. 19, 2019, entitled "SYSTEM, METHOD, AND COMPUTER ALGORITHM AND CHARACTERIZATION AND CLASSIFICATION OF ELECTROPHYSIOLOGICAL EVOKED POTENTIALS," which is a divisional application of U.S. patent application Ser. No. 13/874,867, filed May 1, 2013, entitled "SYSTEM, METHOD, AND COMPUTER ALGORITHM AND CHARACTERIZATION AND CLASSIFICATION OF ELECTROPHYSIOLOGICAL EVOKED POTENTIALS," which claims priority to U.S. Provisional Patent Application Ser. No. 61/641,583 filed May 2, 2012 entitled "SYSTEM, METHOD, AND COMPUTER ALGORITHM FOR CHARACTERIZATION AND CLASSIFICATION OF ELECTROPHYSIOLOGICAL POTENTIALS," each of which is hereby incorporated herein by reference in its entirety.

BACKGROUND OF THE INVENTION

1. Field of the Invention

The present invention relates generally to detecting changes in evoked potentials (EPs), and more particularly to detecting changes in EPs automatically with a computer algorithm.

2. Related Art

Somatosensory evoked potentials are summated electrical potentials usually recorded from the head or neck area after repeatedly stimulating a peripheral nerve. Monitoring patients using somatosensory evoked potentials during surgery has been shown to allow early identification of impending positioning effect injury that can then be avoided by repositioning the patient to alleviate pressure or tension.

For example, as described in Hickey, C.; Gugino, L. D.; Aglio, L. S.; Mark, J. B.; Son, S. L. & Maddi, R. (1993), "Intraoperative somatosensory evoked potential monitoring predicts peripheral nerve injury during cardiac surgery," Anesthesiology 78(1), 29-35, Kamel, I. R.; Drum, E. T.; Koch, S. A.; Whitten, J. A.; Gaughan, J. P.; Barnette, R. E. & Wendling, W. W. (2006), "The use of somatosensory evoked potentials to determine the relationship between patient positioning and impending upper extremity nerve injury during spine surgery: a retrospective analysis," Anesth Analg 102(5), 1538-1542, and Labrom, R. D.; Hoskins, M.; Reilly, C. W.; Tredwell, S. J. & Wong, P. K. H. (2005), and "Clinical usefulness of somatosensory evoked potentials for detection of brachial plexopathy secondary to malpositioning in scoliosis surgery." Spine 30(18), 2089-2093, the above incorporated by reference in their entirety's.

Such monitoring generally requires highly trained technologists under physician supervision with sophisticated, multichannel amplifier and display equipment. Unfortunately, such personnel and equipment are limited in their availability, require pre-booking, and are costly. In addition, such monitoring is not traditionally done in many of the areas in which positioning effects occur outside of the operating room where unresponsive, weak or confined patients may incur positioning effect.

To acquire and record the EPs, a technologist connects electrodes placed on the patient to a neuromonitoring instrument that evokes, acquires, processes and displays the waveforms. Typically, the technologist reviews the waveforms while a neurologist contemporaneously reviews the EP waveforms either on site or remotely through the internet. The technologist and neurologist are trained and are experts in determining whether the changes in the EP waveforms are significant and are indicative of pending nerve injury. The cost of having professionals fully engaged in interpreting these waveforms results in rationing of the service to all but the most high risk surgeries.

U.S. Patent Application Publication No. 2008/0167574 describes a semiautomated device available for automatically measuring biometric signals during surgery to avoid nerve injury. However, the device focuses on muscle or motor recordings to measure nerve proximity to surgical instruments and does not address positioning effect.

The difficulty with analyzing and classifying waveforms to identify positioning effect lies in the wide variation in the amplitude, frequency and shape of the waveforms. These variations are caused by many factors including anesthesia, electrical interference from other devices and any preexisting abnormalities of the nerves.

Accordingly, there is a need for a system and method that can overcome the disadvantages of previous systems and methods.

SUMMARY OF THE INVENTION

In an exemplary embodiment of the present invention, a system, method, and computer algorithm for characterization and classification of electrophysiological EPs is disclosed. An EP may be defined as a voltage versus time signal obtained by a neural system using suitable electrodes. For example when obtaining an EP from a somatosensory system a signal may be obtained by ensemble averaging the electrophysiological responses to repetitive stimulation of the somatosensory system detected using suitable electrodes. Examples of EPs are somatosensory, auditory or visual EPs. The algorithms are applied to a time sequence of EPs acquired over the course of an ongoing clinical procedure. The algorithms establish the characteristics of a baseline/normal EP and then characterize subsequent EPs relative to the baseline EP as well as to previous EPs to determine if the functioning of the underlying sensory neural system has been significantly affected by the ongoing clinical procedure. The algorithms communicate with ancillary hardware and algorithms developed to acquire the sequence of EPs and provide suitable feedback to ensure an effective clinical workflow. The algorithms provide the basis for a clinically effective application such that false positives and false negatives are minimized.

Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

FIG. 2 illustrates an exemplary depiction of a sequence of suitable stimuli applied to a physiological system of interest and the sequence of corresponding responses according to an exemplary embodiment of the present invention.

FIG. 4A illustrates an exemplary flowchart process for acquiring and classifying EP responses according to an exemplary embodiment of the present invention.

FIG. 4B illustrates an exemplary flowchart process for determining whether a change has occurred in a sequence of EPs according to an exemplary embodiment of the present invention.

FIG. 5 illustrates an exemplary flowchart process for calculating a baseline response according to an exemplary embodiment of the present invention.

DETAILED DESCRIPTION OF THE INVENTION

Various exemplary embodiments of the invention including preferred embodiments are discussed in detail below. While specific exemplary embodiments are discussed, it should be understood that this is done for illustration purposes only. A person skilled in the relevant art will recognize that other components and configurations can be used without parting from the spirit and scope of the invention.

An embodiment of the present invention relates to the computer signal processing and pattern recognition algorithms for the characterization and classification of EPs in real-time. This algorithm may substitute for the expert analysis typically provided by the technologist and physician. The computer algorithm running in software installed on an EP machine may be used in any surgery or situation where a patient is at risk to detect, alert and ameliorate positioning effect or any abnormality.

Figure 1:
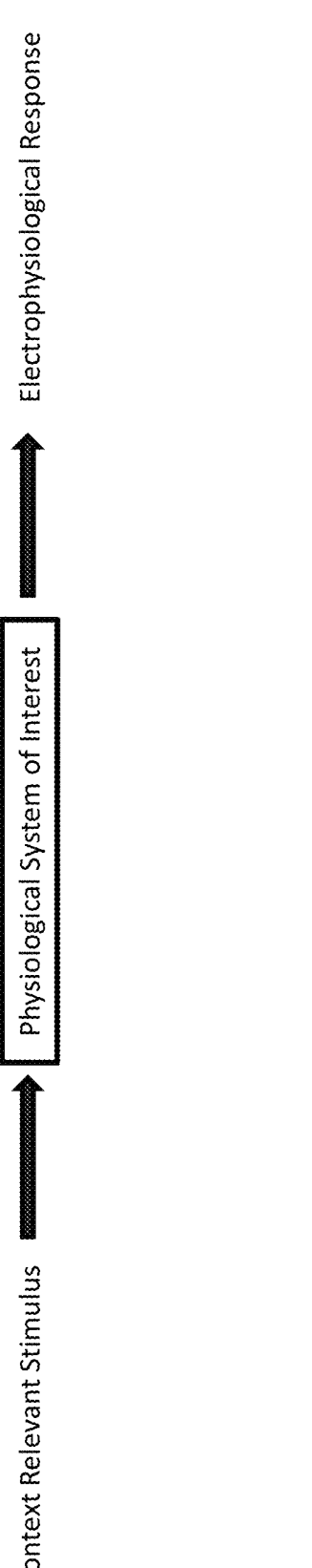
FIG. 1 illustrates an exemplary depiction of stimulation of a physiological system of interest with a context relevant stimulus according to an exemplary embodiment of the present invention.

FIG. 1 illustrates an exemplary stimulation of a physiological system of interest with a context relevant stimulus according to an exemplary embodiment of the present invention. For the somatosensory system, for example, a stimulus may be the application of an appropriate sized and shaped current pulse over a superficial nerve. Given that a suitable stimulus is applied, the electrophysiological response is then a volley of action potentials along the axons excited by the applied stimulus.

FIG. 2 illustrates an exemplary depiction of a sequence of suitable stimuli applied to a physiological system of interest and the sequence of corresponding responses. The sequence of corresponding responses may be detected using suitable electrodes suitably configured at a suitable recording site according to an exemplary embodiment of the present invention. These responses are comprised of time sampled and digitized measurements of the volume conducted voltage fields created by the electrophysiological response of the physiological system of interest when evoked by the applied stimuli.

Figure 3:
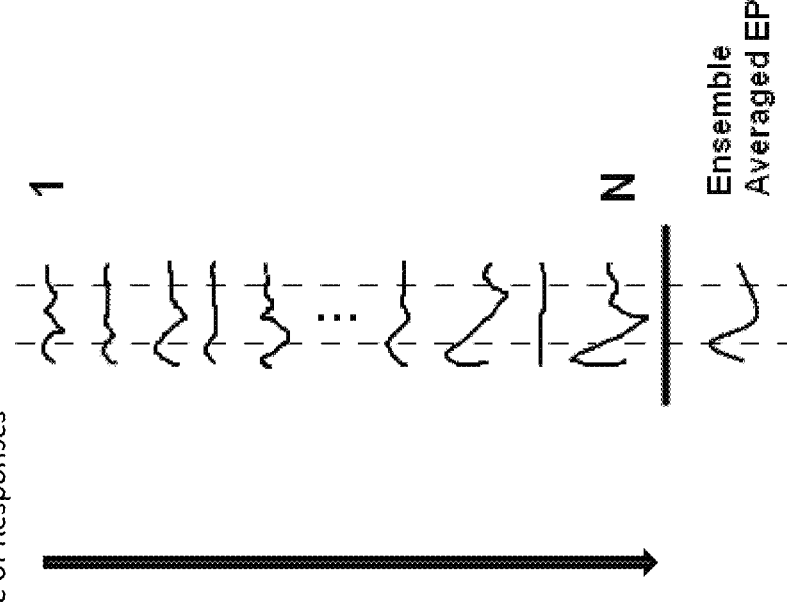
FIG. 3 illustrates an exemplary depiction of the creation of an ensemble averaged EP based on a number of responses according to an exemplary embodiment of the present invention.

FIG. 3 illustrates an exemplary depiction of the creation of an ensemble averaged EP based on a number of responses according to an exemplary embodiment of the present invention. Individual responses may be contaminated by voltage contributions from the electrophysiological activity of other physiological systems as well as ambient electrical noise. As such, in order to obtain a suitable signal to noise ratio, a number of responses may be ensemble averaged to create a resulting evoked potential (EP). The signal to noise ratio of the resulting EP improves as N, the number of responses averaged, increases. In an embodiment, N may range from 10 to 1000 depending on the physiological system of interest.

EPs may be processed to assess the state of the physiological system of interest. A physiological system in a normal operating mode may be considered to be in a "Good" state. If the physiological system is stressed, fatigued, or injured, the system may be considered to be in a "Bad" state. Starting with the physiological system in a Good state, detected changes in the characteristics of the EPs in a sequence of EPs can be used to predict if the physiological system is in a Good or Bad state.

FIG. 4A illustrates an exemplary flowchart process for acquiring and classifying EP responses according to an exemplary embodiment of the present invention. Each EP may be initially filtered to remove unwanted instrumentation noise to better present the electrophysiological response of the system of interest. The EPs may be filtered based on likelihood estimation.

If a baseline response does not exist, acquired responses may be analyzed to estimate a baseline response and to establish an analysis range. For example, if there is not $N_I$ Good responses received, where $N_I$ is a number of initial EP responses required to create a baseline response, then a baseline response may not exist. The analysis to estimate a baseline response and to establish an analysis range is further described below.

If a baseline response exists, the baseline may be updated based on the current response. Updating the baseline is further described below.

Once the current baseline response is determined, the current response is then characterized relative to the current baseline and previous response. For example, characterization may at least one of a Euclidean distance, a pseudo-correlation, a cross-correlation, or an energy ratio between the current response and current baseline. Energy ratio may be the ratio of the energy between the current response and the current baseline. The energy ratio may represent a change in size of the EP response. The current response may be then be classified based on the current response's characterization.

EPs may be classified into four possible categories: Good, Bad, Undetermined and Unreliable based on the characterization. A Good classification may indicate the EP characterization corresponds with no significant waveform change. For example, when there is no positioning effect. A Bad classification may indicate the EP characterization corresponds with a signification waveform change. For example, when there is positioning effect. An Undetermined classification may indicate that the EP characterization may be of indeterminate significance. For example, the EP characterization may be insufficient for a Good classification but also insufficient for a Bad classification. For example, the EP may possibly correspond with either positioning effect or no positioning effect. An unreliable classification may indicate the EP includes too much noise to be properly characterized and classified.

Each classification may correspond with a particular threshold. The threshold may indicate how similar an EP response should be to a baseline to be considered a Good response or how dissimilar an EP response should be to a baseline to be considered a Bad response. The thresholds may be based on the characterizations of the EP responses. For example, thresholds may be based on at least one of Euclidean distance, a pseudo-correlation, a cross-correlation, or an energy ratio between an EP response and a baseline. A threshold may also indicate how much noise may be included in an EP response before the EP response is considered unreliable.

The thresholds used for classification may be determined by analyzing training data. Training data may include a plurality of EP responses known to correspond to particular classifications. Using multiple sets of thresholds determined from the analysis of training data, the current response may be classified as belonging to a category of interest based on the values of its calculated metrics.

FIG. 4B illustrates an exemplary flowchart process for determining whether a change has occurred in a sequence of EPs according to an exemplary embodiment of the present invention. FIG. 4B continues from FIG. 4A. Given the sequence of classified EPs, it may be determined whether the state of the physiological system of interest has changed (either from Good to Bad or vice versa) or if the state of the physiological system of interest has not changed. If the state has changed, the system may create an alert.

FIG. 5 illustrates an exemplary flowchart process for calculating a baseline response according to an exemplary embodiment of the present invention. Currently loaded responses may be iteratively represented as nodes within a minimum spanning tree (MST) created using the Euclidean distances between response pairs. Each line in the MST that links pairs of responses may represent a Euclidean distance value. The currently loaded responses may be initially acquired responses. Response pairs may be combinations of any two currently loaded responses. For example, three responses may result in three response pairs. The Euclidean distance may be based on the sum of the squares of the differences between responses in each response pair or the sum of the absolute value of the differences between responses in each response pair.

The MST may be separated into clusters based on cutting lines that are greater than a threshold. The threshold may be based on the mean of the line lengths and standard deviations of the line lengths. The clusters may be sorted based on the sizes of the clusters. The size of a cluster may be the number of responses within the cluster. The cluster with the largest size may be selected so that a temporary baseline is calculated based on the responses within the cluster. All the responses within the largest cluster may be aligned using a default analysis range and pseudo-correlation. The response members of the cluster with the largest number of members may be averaged to estimate the baseline response.

Figure 6:
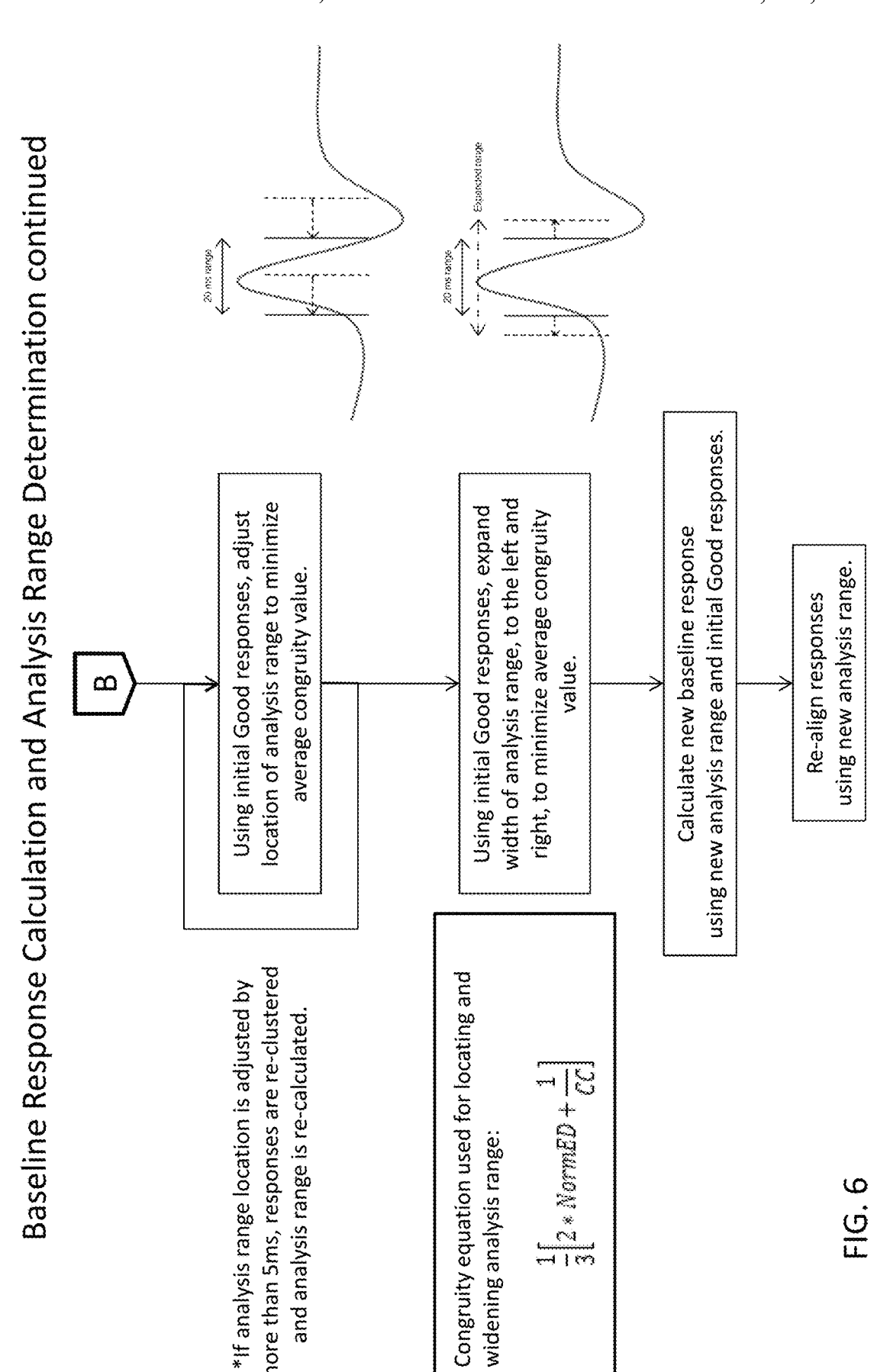
FIG. 6 illustrates an exemplary flowchart process for determining the analysis range according to an exemplary embodiment of the present invention.

FIG. 6 illustrates an exemplary flowchart process for determining the analysis range according to an exemplary embodiment of the present invention. Initial responses are characterized and classified using initial baseline response estimates and a default analysis range. First, initial Good responses are used to locate a default width analysis range by adjusting the location of the range until a minimum congruity value is obtained. Using the initial Good responses, the width of the analysis range is then adjusted by increasing it to the left or right until a minimum congruity value is obtained. For both analysis range location and sizing, the congruity measure may be:

$$\frac{1}{3}\left[2 * NormED + \frac{1}{CC}\right]$$

where NormED is a normalized Euclidean distance and CC is the cross-correlation. While not shown in FIG. 6, the calculated new baseline response may be used to re-calculate the analysis range.

Figure 7:
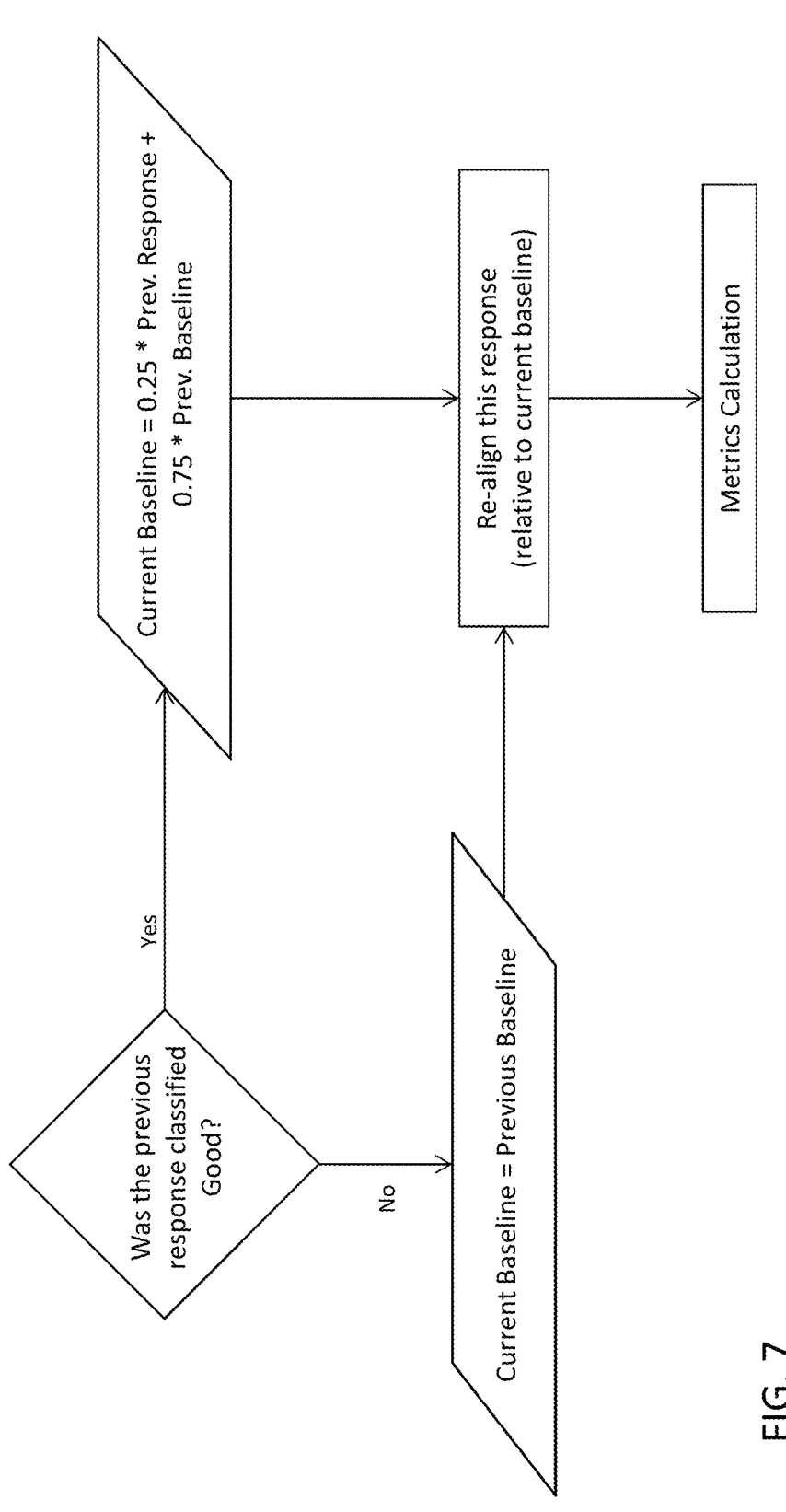
FIG. 7 illustrates an exemplary flowchart process for updating a baseline response according to an exemplary embodiment of the present invention.

FIG. 7 illustrates an exemplary flowchart process for updating a baseline response according to an exemplary embodiment of the present invention. As shown in FIG. 7, if a previous response is classified as good, the current baseline may be recalculated based on the previous response and the previous baseline. For example, the current baseline may be set to 25% of the previous response and 75% of the previous baseline. If the previous response is not classified as good, the current baseline may be set to the previous baseline.

Regardless of how the new current baseline is determined, the new current baseline may be used to re-align the current response relative to the new current baseline. Metric calculation may then be performed on the re-aligned response.

Figure 8:
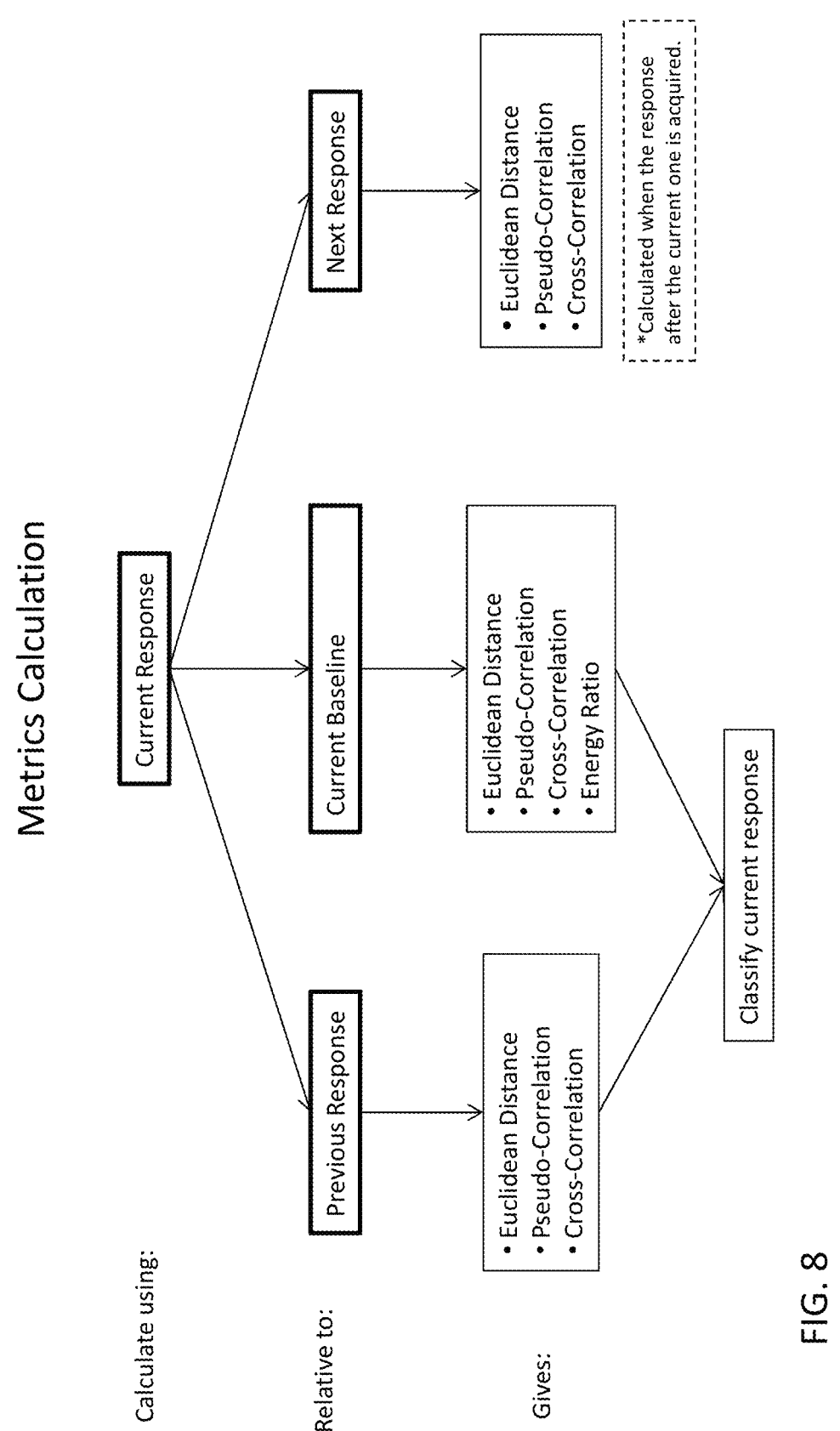
FIG. 8 illustrates an exemplary embodiment of a relationship diagram in metric calculation for characterizing EPs according to an exemplary embodiment of the present invention.

FIG. 8 illustrates an exemplary embodiment of a relationship diagram in metric calculation for characterizing EPs according to an exemplary embodiment of the present invention. As shown in FIG. 8, a current response may be compared with a previous response to give a Euclidean distance between the responses, a pseudo-correlation, and a cross-correlation. A current response may be compared with a current baseline to give a Euclidean distance between the response and baseline, a pseudo-correlation, a cross-correlation, and an energy ratio. The current response may be classified based on these various results.

After a next response is acquired, the current response may also be used to give a Euclidean distance between the current response and next response, a pseudo-correlation, and a cross-correlation.

Figure 9:
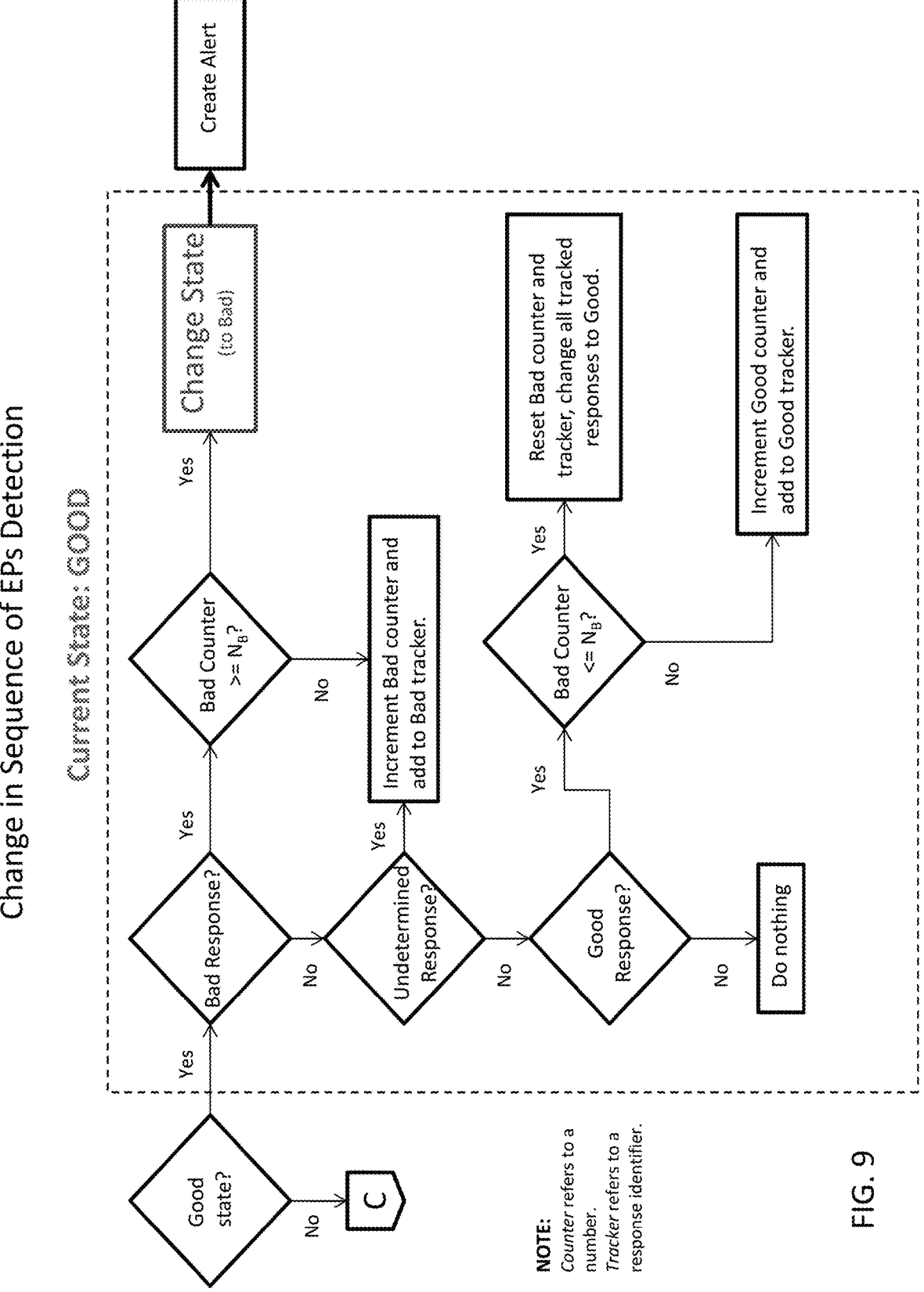
FIG. 9 illustrates an exemplary flowchart process for a good state according to an exemplary embodiment of the present invention.

FIG. 9 illustrates an exemplary flowchart process for a good state according to an exemplary embodiment of the present invention. If a Bad response is received while in the Good state, the system may check to see if a bad counter is greater than or equal to a bad counter threshold, $N_B$. The bad counter may indicate a number of Bad responses. The bad counter threshold $N_B$ may indicate the number of Bad responses or undetermined responses to receive before the next Bad response changes the state to a bad state. The bad counter threshold $N_B$ may be set for each state depending on the physiological system of interest.

If the bad counter is greater than the bad counter threshold $N_B$, then the current state may be changed to the Bad state and an alert may be created. The alert may be conveyed to a user of the system in a variety of ways, e.g., with displaying visualizations, generating sounds, creating vibrations, etc. If the bad counter is not greater than bad counter threshold $N_B$, then the bad counter may be incremented and the Bad response added to a bad tracker. The bad tracker may track the Bad responses and Undetermined responses received.

If the response received is not a bad response, the system may check if the response received is an undetermined response. If the response received is an undetermined response, then the bad counter is also incremented and the undetermined response is added to the bad tracker.

If the response received is also not an undetermined response, the system may check if the response received is a good response. If the response received is a good response, then if the bad counter is less than or equal to the bad counter threshold $N_B$, then the bad counter is reset to zero and the bad tracker is emptied. If the bad counter is greater than bad counter threshold $N_B$, then the good counter may be incremented and the Good response added to the Good tracker.

If the response received is also not a good response, then the system may determine that the response is an unreliable response and may ignore the response.

Based on the bad counter, the bad tracker, the good counter, and the good tracker, the system may provide different indications to a user. The system may change the color of an icon displayed so that the icon appears green when the bad counter is zero and gradually becomes redder with increasing values for the bad tracker.

Figure 10:
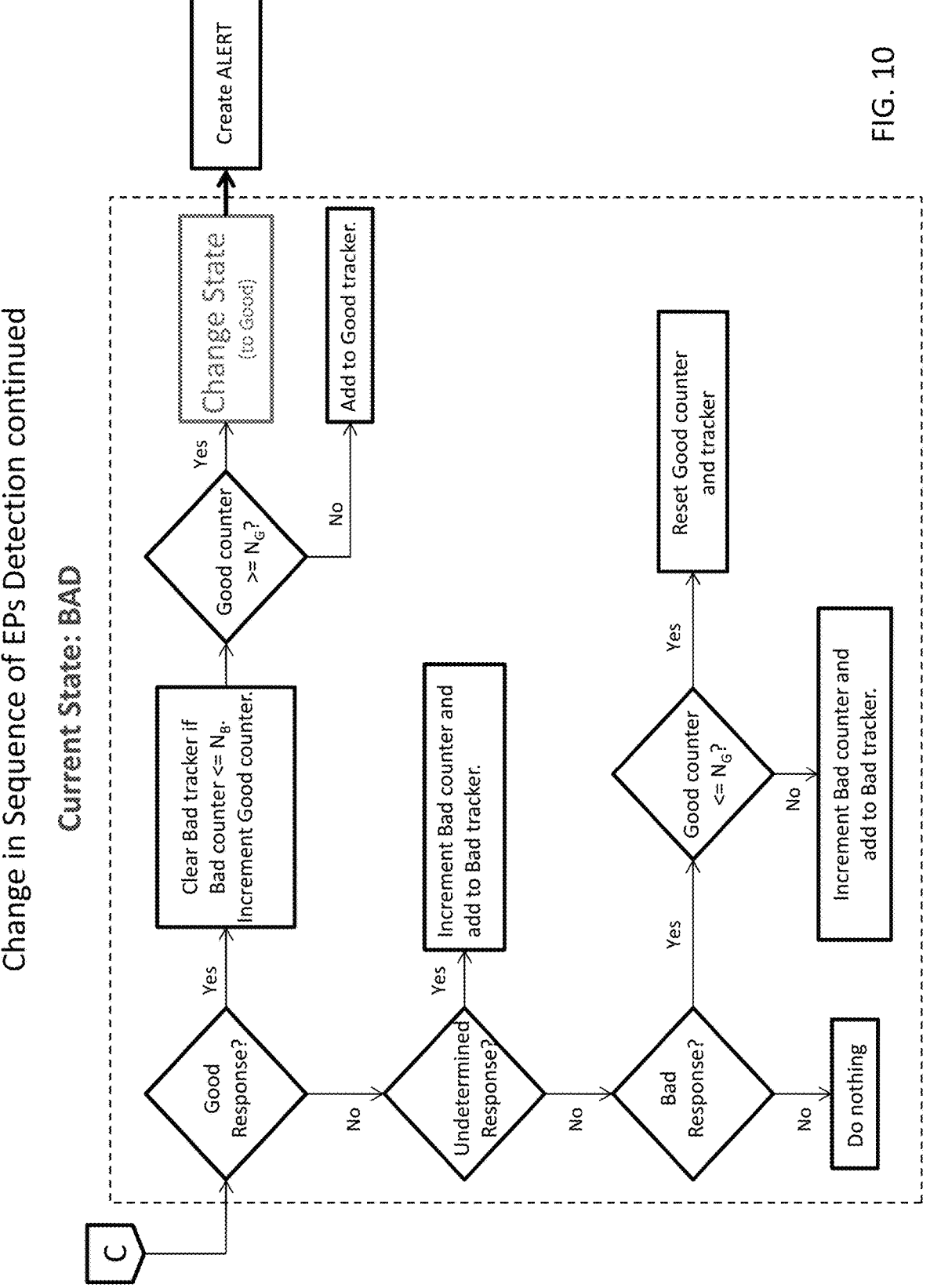
FIG. 10 illustrates an exemplary flowchart process for a bad state according to an exemplary embodiment of the present invention.

FIG. 10 illustrates an exemplary flowchart process for a bad state according to an exemplary embodiment of the present invention. If a good response is received while in the bad state, the system may increment a good counter, and, if the bad counter is less than the bad counter threshold $N_B$, clear the bad tracker check.

The system may check to see if a good counter is greater than or equal to a good counter threshold, $N_G$. The good counter may indicate a number of good responses. The good counter threshold $N_G$ may indicate the number of good responses needed to be received to change the state to a good state. The good counter threshold $N_G$ may be set for each state depending on the physiological system of interest. If the good counter is greater than the good counter threshold $N_G$, then the current state may be changed to the good state and an alert may be created. If the good counter is not greater than good counter threshold $N_G$, then the good response may be added to a good tracker. The good tracker may track the good responses received.

If the response received is not a good response, the system may check if the response received is an undetermined response. If the response received is an undetermined response, then the bad counter is incremented and the undetermined response is added to the bad tracker.

If the response received is also not an undetermined response, the system may check if the response received is a bad response. If the response received is a bad response, then if the good counter is less than or equal to the good counter threshold $N_G$, then the good counter is reset to zero and the good tracker is emptied. If the good counter is greater than good counter threshold $N_G$, then the bad counter may be incremented and the bad response added to the bad tracker.

If the response received is also not a bad response, then the system may determine that the response is an unreliable response and may ignore the response.

The signal processing routines may be applied to reduce the noise in the acquired EPs and to detect when EPs with inadequate signal to noise ratio (SNR) are acquired so that these EPs may be excluded from further analysis and the poor signal quality reported. The number of unreliable signals received may be tracked and compared with a threshold to determine when to create an alert regarding poor signal quality.

The filtering techniques applied may use likelihood-estimation based averaging to decrease instrumentation and context-based noise and increase the SNR of the acquired EPs such that baseline EPs can be more clearly defined and that changes in subsequent EPs can be better characterized and compared to the baseline and previous EPs.

Pattern recognition algorithms may be used to characterize the EPs, to measure changes in latter acquired EPs relative to the baseline and previous EPs and to detect when changes to the EPs, indicative of a changed functioning of the underlying sensory neural system, have occurred. EPs may be characterized using their energy, Euclidean distance and pseudo and cross correlations relative to a defined baseline template response as well as to previous EPs. Using these metrics, classification rules may be applied to determine if the current response indicates significant (adverse or recovering) changes to the underlying physiological system generating the EPs.

In an embodiment, a component may be added to allow medical or other attending personnel to reset the baseline response when the changes in the acquired EPs are not related to any underlying physiological change (e.g., changes related to stimulation or electrode factors).

In an embodiment, the system may be an automated EP analysis apparatus for monitoring, detecting and identifying changes (adverse or recovering) to a physiological system generating the analyzed EPs, wherein the apparatus is adapted to characterize and classify EPs and create alerts of changes (adverse or recovering) to the physiological systems generating the EPs if the acquired EP waveforms change significantly in latency, amplitude or morphology. The system may further include a system to integrate such apparatus into other devices in a surgical environment.

The apparatus may also feed information to other devices in the surgical environment that allows these devices to manually or automatically ameliorate or mitigate the physiological changes and improve subsequently acquired EP waveforms.

The apparatus may also obtain information from an anesthesia or blood pressure machine to calculate when changes in EP waveforms are due to anesthesia or blood pressure changes.

The apparatus may perform a method of automatically identifying potential injury to peripheral nerve structures including stimulating peripheral nerves with electrical pulses, recording resultant electrical waveforms generated by the nervous system through electrodes placed at the neck or head, measuring changes or trends in the acquired EP waveforms, alerting the user to the changes, allowing the user the option to decide if the data is accurate, passing that information to an automated operating room table, and automatically or semi automatically readjusting patient position through adjustment of the table to ameliorate or avoid injury.

While various embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

What is claimed is:

1. An automated evoked potential (EP) analysis apparatus for automatic monitoring, detecting, and identifying of changes (adverse or recovering) to a physiological system generating EP waveforms, wherein the apparatus is adapted to:

analyze the signal-to-noise ratio of acquired EP waveforms;

update the baseline using EP waveforms that are analyzed to have an adequate signal-to-noise ratio;

exclude each EP waveform having an inadequate signal-to-noise ratio;

track the number of inadequate EP waveforms; and generate an alert if the number of inadequate EP waveforms exceeds a threshold.

2. The apparatus of claim 1, wherein the analyzing the signal-to-noise ratio of acquired EP waveforms is achieved using likelihood estimation-based averaging.

3. The apparatus of claim 1, wherein the apparatus is further adapted to automatically acquire and establish the baseline using real-time EP waveforms.

4. The apparatus of claim 1, wherein the apparatus is further adapted to characterize and classify the EP waveforms and create alerts of the changes (adverse or recovering) to the physiological system generating the EP waveforms if the acquired EP waveforms change significantly in latency, amplitude or morphology relative to a baseline.

5. The apparatus of claim 1, further comprising a system to integrate the apparatus into other devices in a surgical environment.

6. The apparatus of claim 1, wherein said apparatus is configured to feed information to other devices in a surgical environment to thereby allow the other devices to manually or automatically ameliorate or mitigate the changes and improve subsequently acquired EP waveforms.

7. The apparatus in claim 1, wherein said apparatus is configured to obtain information from an anesthesia or blood pressure machine to calculate when changes in the EP waveforms are due to anesthesia or blood pressure changes.

8. The apparatus of claim 1, wherein the apparatus comprises memory and a processor, wherein the processor is configured to execute instructions stored on the memory, that, when executed by the processor, cause the processor to perform operations comprising:

stimulating, via electrical pulse electrodes, a peripheral nerve structure;

recording, via electrodes placed at the neck or head, signals forming a resultant electrical (EP) waveform generated by the nervous system in response to the stimulation;

measuring a waveform change in the recorded EP waveform relative to a baseline response, the waveform change comprising a Euclidean distance, a pseudo-correlation, a cross-correlation, and an energy ratio between the recorded EP waveform and the baseline response;

comparing the waveform change with one or more threshold change values to classify the recorded EP waveform; and determining whether a current state of the peripheral nerve structure has changed based on the classification of the recorded EP waveform by determining whether a count of EP waveforms in a classification exceeds a threshold count value.

9. The apparatus of claim 8, wherein the operations further comprise:

alerting a user to the waveform changes; and providing the user with an option to decide if data associated with the waveform changes is accurate.

10. The apparatus of claim 8, wherein the operations further comprise:

transmitting the current state to an automated operating room table; and automatically or semi automatically readjusting a patient position through adjustment of the table to ameliorate or avoid injury.

11. The apparatus of claim 8, wherein the waveform change comprises a Euclidean distance and at least one from a group consisting of: a pseudo-correlation, a cross-correlation, and an energy ratio between the recorded EP waveform and the baseline response.

12. The apparatus of claim 8, wherein the operations further comprise classifying the recorded EP waveform into four possible categories: good, bad, undetermined, and unreliable based on the change relative to the baseline response.

13. The apparatus of claim 12, wherein the threshold change value for a good classification relates to how similar the recorded EP waveform should be to the baseline response.

14. The apparatus of claim 8, wherein a threshold change value relates to how similar the recorded EP waveform should be to the baseline response.

15. The apparatus of claim 8, wherein determining whether the count of EP waveforms in the classification exceeds the threshold count value comprises:

counting a number of EP responses that are classified in a given classification;

comparing the current count to the threshold count value; and if the current count exceeds the threshold count value, changing the state of the peripheral nerve structure to the state that corresponds with the exceeded threshold count value.

16. The apparatus of claim 8, wherein the operations further comprise generating an alert if the current state of the peripheral nerve structure has changed.

* * * * *